United States Patent [19]
Ishii et al.

[11] Patent Number: 6,143,924
[45] Date of Patent: Nov. 7, 2000

[54] PROCESS FOR PRODUCING ORGANIC SULFUR ACIDS OR SALTS THEREOF

[75] Inventors: Yasutaka Ishii, Takatsuki; Tatsuya Nakano, Himeji, both of Japan

[73] Assignee: Daicel Chemical Industries, LTD, Osaka, Japan

[21] Appl. No.: 09/522,140

[22] Filed: Mar. 9, 2000

[30] Foreign Application Priority Data

Mar. 9, 1999 [JP] Japan .................................. 11-62443

[51] Int. Cl.$^7$ ............................................. C07C 309/00
[52] U.S. Cl. ........................................................ 562/100
[58] Field of Search ............................................. 562/100

[56] References Cited

U.S. PATENT DOCUMENTS 2,220,678  11/1940  Cromwell et al. ...................... 562/100

*Primary Examiner*—Joseph K. McKane
*Assistant Examiner*—Joseph Murray
*Attorney, Agent, or Firm*—Birch, Stewart, Kolasch & Birch, LLP

[57] ABSTRACT

In the presence of an imide compound of the following formula (1), a sulfur oxide is reacted with an organic substrate to yield a corresponding sulfur acid or its salt. This process can efficiently produce an organic sulfur acid or its salt under relatively mild conditions.

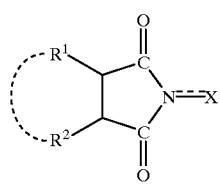

(I)

wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond or an aromatic or non-aromatic ring; X is an oxygen atom or a hydroxyl group, where one or two N-substituted cyclic imido groups indicated in the formula (1) may be further bonded to the aforementioned $R^1$, $R^2$ or to the double bond or aromatic or non-aromatic ring formed together by $R^1$ and $R^2$.

3 Claims, No Drawings

PROCESS FOR PRODUCING ORGANIC SULFUR ACIDS OR SALTS THEREOF

BACKGROUND OF THE INVENTION

1. Field of the Invention

The present invention relates to a process for producing organic sulfur acids or salts thereof which are useful as, for example, materials for pharmaceuticals, agrochemicals and dyestuffs, or as detergents.

2. Description of the Related Art

A variety of processes are known for producing organic sulfur acids and salts thereof. For example, sulfonic acids can be obtained by a process of oxidizing a thiol or disulfide with an oxidizing agent, a process of reacting an aromatic hydrocarbon with anhydrous $SO_3$-pyridine or chlorosulfuric acid by the use of Friedel-Crafts reaction, and a process of subjecting an unsaturated compound to free radical addition. These processes, however, require extreme reaction conditions or inevitably produce large amounts of by-products. Separately, a process for directly and efficiently sulfonating non-aromatic hydrocarbons has not yet been known.

SUMMARY OF THE INVENTION

Accordingly, an object of the present invention is to provide a process for efficiently producing an organic sulfur acid or its salt under relatively mild conditions.

Another object of the invention is to provide a process for efficiently producing a corresponding organic sulfur acid or its salt directly from a non-aromatic hydrocarbon.

After intensive investigations, the present inventors found that a combination use of a specific imide compound and a sulfur oxide can efficiently produce corresponding organic sulfur acids or salts thereof from a variety of substrates. The present invention has been accomplished on the basis of these findings.

Specifically, the invention provides a process for producing an organic sulfur acid or its salt. The process includes the step of reacting a sulfur oxide with an organic substrate in the presence of an imide compound of the following formula (1):

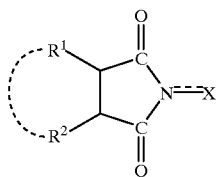

(I)

wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond, or an aromatic or non-aromatic ring; X is an oxygen atom or a hydroxyl group, where one or two N-substituted cyclic imido groups indicated in the formula (1) may be further bonded to the aforementioned $R^1$, $R^2$, or to the double bond or aromatic or non-aromatic ring formed together by $R^1$ and $R^2$, to yield a corresponding organic sulfur acid or its salt.

In the above process, the sulfur oxide may mainly contain at least one selected from sulfur dioxide and sulfur trioxide. The organic substrate may be preferably any of (a) isocyclic or heterocyclic compounds each having a methylene group, (b) compounds each having a methine carbon atom, and (c) compounds each having a methyl group or a methylene group at the adjacent position to an unsaturated bond.

DESCRIPTION OF THE PREFERRED EMBODIMENT

[Imide Compound]

The imide compounds of the formula (1) are for use as a catalyst in the invented process. Of the substituents $R^1$ and $R^2$ in the formula (1), the halogen atom includes iodine, bromine, chlorine and fluorine atoms. The alkyl group includes, for example, methyl, ethyl, propyl, isopropyl, butyl, isobutyl, s-butyl, t-butyl, pentyl, hexyl, heptyl, octyl, decyl, and other straight- or branched-chain alkyl groups each having about 1 to 10 carbon atoms. Preferred alkyl groups are alkyl groups each having about 1 to 6 carbon atoms, and are more preferably lower alkyl groups each having about 1 to 4 carbon atoms.

The aryl group includes phenyl, and naphthyl groups, for example; and the illustrative cycloalkyl group includes cyclopentyl, and cyclohexyl groups. As the alkoxy group, there may be mentioned, for example, methoxy, ethoxy, propoxy, isopropoxy, butoxy, isobutoxy, t-butoxy, pentyloxy, hexyloxy, and other alkoxy groups each having about 1 to 10 carbon atoms, preferably about 1 to 6 carbon atoms, of which lower alkoxy groups each having about 1 to 4 carbon atoms are especially preferred.

Examples of the alkoxycarbonyl group include methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, and other alkoxycarbonyl groups each having about 1 to 10 carbon atoms in the alkoxy moiety. Preferred alkoxycarbonyl groups are alkoxycarbonyl groups each having about 1 to 6 carbon atoms in the alkoxy moiety, and are especially lower alkoxycarbonyl groups each having about 1 to 4 carbon atoms in the alkoxy moiety.

The illustrative acyl groups include, but are not limited to, formyl, acetyl, propionyl, butyryl, isobutyryl, valeryl, isovaleryl, pivaloyl, and other acyl groups each having about 1 to 6 carbon atoms.

The substituents $R^1$ and $R^2$ maybe identical to, or different from, each other. The substituents $R^1$ and $R^2$ in the formula (1) may be combined to form a double bond or an aromatic or non-aromatic ring. The preferred aromatic or non-aromatic ring is a 5- to 12-membered ring, and especially a 6- to 10-membered ring. The ring may be a heterocyclic ring or a condensed heterocyclic ring, but it is often a hydrocarbon ring. Such rings include, for example, non-aromatic alicyclic rings (e.g., cyclohexane ring and other cycloalkane rings which may have a substituent, cyclohexene ring and other cycloalkene rings which may have a substituent), non-aromatic bridged rings (e.g., 5-norbornene ring and other bridged hydrocarbon rings which may have a substituent), benzene ring, naphthalene ring and other aromatic rings (including condensed rings) which may have a substituent. The ring is composed of an aromatic ring in many cases. The ring may have a substituent such as an alkyl group, a haloalkyl group, a hydroxyl group, an alkoxy group, a carboxyl group, an alkoxycarbonyl group, an acyl group, a nitro group, a cyano group, an amino group, or a halogen atom.

In the formula (1), X represents an oxygen atom or a hydroxyl group, and the bond between the nitrogen atom N and X is a single bond or a double bond.

To $R^1$, $R^2$ or to the double bond or aromatic or non-aromatic ring formed together by $R^1$ and $R^2$, one or two N-substituted cyclic imido groups indicated in the formula (1) maybe further bonded. For example, when $R^1$ or $R^2$ is an alkyl group having two or more inclusive carbon atoms, the N-substituted cyclic imido group may be formed together with adjacent two carbon atoms constituting the alkyl group. Likewise, when $R^1$ and $R^2$ are combined to form a double bond, the N-substituted cyclic imido group may be formed together with the double bond. When $R^1$ and $R^2$ are combined to form an aromatic or non-aromatic ring, the N-substituted cyclic imido group may be formed with adjacent two carbon atoms constituting the aforementioned ring.

Preferred imide compounds include compounds of the following formulae:

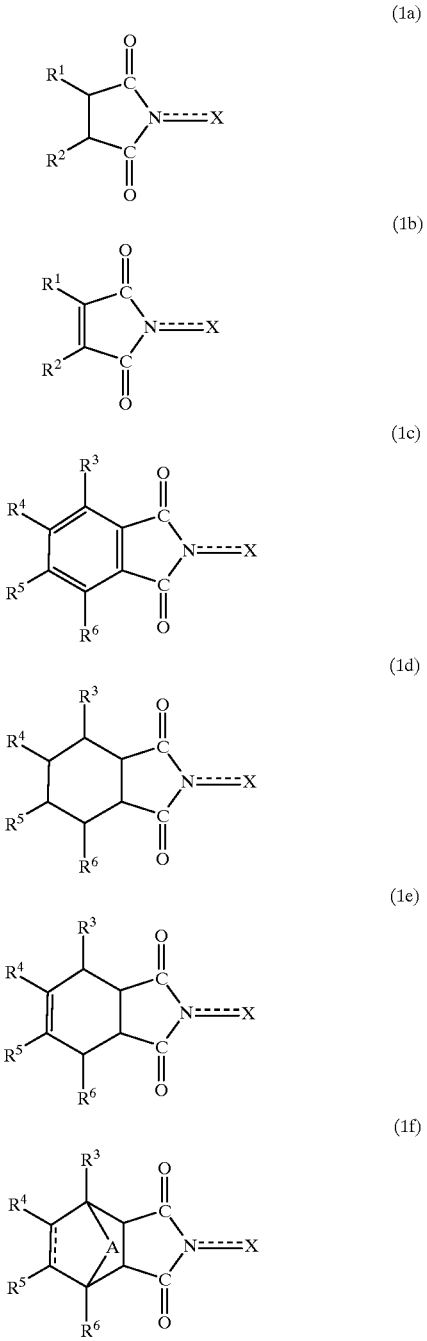

wherein $R^3$ to $R^6$ are each, identical to or different from each other, a hydrogen atom, an alkyl group, a haloalkyl group, a hydroxyl group, an alkoxy group, a carboxyl group, an alkoxycarbonyl group, an acyl group, a nitro group, a cyano group, an amino group, or a halogen atom, where adjacent groups of $R^3$ to $R^6$ may be combined to form an aromatic or non-aromatic ring; in the formula (1f), A represents a methylene group or an oxygen atom, and $R^1$, $R^2$ and X have the same meanings as defined above, where one or two N-substituted cyclic imido groups indicated in the formula (1c) may be further bonded to the benzene ring in the formula (1c).

In the substituents $R^3$ to $R^6$, the alkyl group includes similar alkyl groups to those exemplified above, especially alkyl groups each having about 1 to 6 carbon atoms. The haloalkyl group includes trifluoromethyl group and other haloalkyl groups each having about 1 to 4 carbon atoms, and the alkoxy group includes similar alkoxy groups to those mentioned above, and especially lower alkoxy groups each having about 1 to 4 carbon atoms. The alkoxycarbonyl group includes similar alkoxycarbonyl groups to those described above, particularly lower alkoxycarbonyl groups each having about 1 to 4 carbon atoms in the alkoxy moiety. As the acyl group, there may be mentioned similar acyl groups to those described above, especially acyl groups each having about 1 to 6 carbon atoms, and the illustrative halogen atoms include fluorine, chlorine and bromine atoms. Each of the substituents $R^3$ to $R^6$ is often a hydrogen atom, a lower alkyl group having about 1 to 4 carbon atoms, a carboxyl group, a nitro group, or a halogen atom. The ring formed together by $R^3$ to $R^6$ includes similar rings to the aforementioned rings which are formed together by $R^1$ and $R^2$. Among them, aromatic or non-aromatic 5- to 12-membered rings are particularly preferred.

Illustrative preferred imide compounds include N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxychlorendimide, N-hydroxyhimimide, N-hydroxytrimellitimide, N,N'-dihydroxypyromellitimide, and N,N'-dihydroxynaphthalenetetracarboximide.

The imide compounds of the formula (1) can be prepared by a conventional imidation process (a process for the formation of an imide), such as a process comprising the steps of allowing a corresponding acid anhydride to react with hydroxylamine $NH_2OH$ for ring-opening of an acid anhydride group, and closing the ring to form an imide.

Such acid anhydrides include, but are not limited to, succinic anhydride, maleic anhydride, and other saturated or unsaturated aliphatic dicarboxylic anhydrides, tetrahydrophthalic anhydride, hexahydrophthalic anhydride (1,2-cyclohexanedicarboxylic anhydride), 1,2,3,4-cyclohexanetetracarboxylic 1,2-anhydride, and other saturated or unsaturated non-aromatic cyclic polycarboxylic anhydrides (alicyclic polycarboxylic anhydrides), HET anhydride (chlorendic anhydride), himic anhydride, and other bridged cyclic polycarboxylic anhydride (alicyclic polycarboxylic anhydrides), phthalic anhydride, tetrabromophthalic anhydride, tetrachlorophthalic anhydride nitrophthalic anhydride, trimellitic anhydride, methylcyclohexenetricarboxylic anhydride, pyromellitic anhydride, mellitic anhydride, 1,8;4,5-naphthalenetetracarboxylic dianhydride, and other aromatic polycarboxylic anhydrides.

Typically preferred imide compounds include N-hydroxyimide compounds derived from alicyclic polycarboxylic anhydrides or aromatic polycarboxylic anhydrides, of which N-hydroxyphthalimide and other N-hydroxyimide compounds derived from aromatic polycarboxylic anhydrides are especially preferred.

Each of the imide compounds of the formula (1) can be used alone or in combination. The imide compounds can be used as being supported by carriers. As such carriers, activated carbon, zeolite, silica, silica-alumina, bentonite, and other porous carries are often employed.

The amount of the imide compound can be selected within a wide range, and is, for example, from about 0.0001 to 1 mole, preferably from about 0.001 to 0.5 mole, and more preferably from about 0.01 to 0.4 mole relative to 1 mole of the substrate. The imide compound is generally used in an amount ranging from about 0.05 to 0.35 mole relative to 1 mole of the substrate.

[Promoter (Co-catalyst)]

In the inventive process, a promoter (co-catalyst) can be used in combination with the catalyst of the formula (1) to improve or enhance the rate and selectivity of the reaction. Such promoters include, but are not limited to, (i) metallic compounds, and (ii) organic salts each composed of a polyatomic cation or a polyatomic anion and its counter ion, which polyatomic cation or anion contains a Group 15 or Group 16 element of the Periodic Table of Elements having at least one organic group bonded thereto. Each of these promoters can be used alone or in combination.

Metallic elements for constituting the metallic compounds (i) are not critical and can be any of metallic elements of the Groups 1 to 15 of the Periodic Table of Elements. The term "metallic element" as used herein also includes boron, B. Examples of the metallic elements include, of the Periodic Table of Elements, Group 1 elements (e.g., Li, Na, K), Group 2 elements (e.g., Mg, Ca, Sr, Ba), Groups 3 elements (e.g., Sc, lanthanoid elements, actinoid elements), Group 4 elements (e.g., Ti, Zr, Hf), Group 5 elements (e.g., V), Group 6elements (e.g., Cr, Mo, W), Group 7 elements (e.g., Mn), Group 8 elements (e.g., Fe, Ru), Group 9 elements (e.g., Co, Rh), Group 10 elements (e.g., Ni, Pd, Pt), Group 11 elements (e.g., Cu), Group 12 elements (e.g., Zn), Groups 13 elements (e.g., B, Al, In), Group 14 elements (e.g., Sn, Pb), and Group 15 elements (e.g., Sb, Bi). Preferred metallic elements include transition metal elements (elements of Groups 3 to 12 of the Periodic Table of Elements). Among them, elements of the Groups 5 to 11 of the Periodic Table of Elements are preferred. The valence of the metallic element is not critical, and may be about 0 to 6, and is about 2 or 3 in many cases.

The metallic compounds (i) include, but are not limited to, elementary substances, hydroxides, oxides (including complex oxides), halides (fluorides, chlorides, bromides, and iodides), salts of oxoacids (e.g., nirates, sulfates, phosphates, borates, and carbonates), oxoacids, isopolyacids, heteropolyacids, and other inorganic compounds of the aforementioned metallic elements; salts of organic acids (e.g., salts of acetic acid, propionic acid, hydrocyanic acid, naphthenic acid, and stearic acid), complexes, and other organic compounds of the metallic elements. Ligands for constituting the complexes include OH (hydroxo), alkoxy groups (e.g., methoxy, ethoxy, propoxy, and butoxy groups), acyl groups (e.g., acetyl, and propionyl groups), alkoxycarbonyl groups (e.g., methoxycarbonyl, and ethoxycarbonyl groups), acetylacetonato, cyclopentadienyl group, halogen atoms (e.g., chlorine and bromine atoms), CO, CN, oxygen atom, $H_2O$ (aquo), phosphines (e.g., triphenylphosphine and other triarylphosphines), and other phosphorus compounds, $NH_3$ (ammine), NO, $NO_2$ (nitro), $NO_3$ (nitrato), ethylenediamine, diethylenetriamine, pyridine, phenanthroline, and other nitrogen-containing compounds.

Concrete examples of the metallic compound (i) include, by taking cobalt compounds as example, cobalt hydroxide, cobalt oxide, cobalt chloride, cobalt bromide, cobalt nitrate, cobalt sulfate, cobalt phosphate, and other inorganic compounds; cobalt acetate, cobalt naphthenate, cobalt stearate, and other salts of organic acids; cobalt acetylacetonato, and other complexes, and other divalent or trivalent cobalt compounds. As illustrative vanadium compounds, there may be mentioned vanadium hydroxide, vanadium oxide, vanadium chloride, vanadyl chloride, vanadium sulfate, vanadyl sulfate, sodium vanadate, and other inorganic compounds; vanadium acetylacetonato, vanadyl acetylacetonato, and other complexes, and other vanadium compounds having a valence of 2 to 5. Examples of compounds of the other metallic elements include compounds corresponding to the above-mentioned cobalt or vanadium compounds. Each of the metallic compounds (i) can be used alone or in combination.

The proportion of the metallic compound (i) is, for example, about 0.0001 to 0.7 mole, preferably about 0.001 to 0.5 mole, and more preferably about 0.0015 to 0.1 mole relative to 1 mole of the substrate. The metallic compound (i) is often used in a proportion of about 0.0015 to 0.05 mole relative to 1 mole of the substrate.

In the organic salts (ii), the Group 15 elements of the Periodic Table of Elements include N, P, As, Sb, and Bi, and the Group 16 elements of the Periodic Table of Elements include, for example, O, S, Se and Te. Preferred elements are N, P, As, Sb, and S, of which N, P, and S are typically preferred.

The organic groups to be bonded to atoms of the elements include, for example, hydrocarbon groups which may have a substituent, and substituted oxy groups. The hydrocarbon groups include, but are not limited to, methyl, ethyl, propyl, isopropyl, butyl, isobutyl, s-butyl, t-butyl, pentyl, hexyl, octyl, decyl, tetradecyl, hexadecyl, octadecyl, allyl, and other straight- or branched-chain aliphatic hydrocarbon groups (alkyl groups, alkenyl groups and alkynyl groups) each having about 1 to 30 carbon atoms (preferably about 1 to 20 carbon atoms); cyclopentyl, cyclohexyl, and other alicyclic hydrocarbon groups each having about 3 to 8 carbon atoms; and phenyl, naphthyl, and other aromatic hydrocarbon groups each having about 6 to 14 carbon atoms. Substituents which the hydrocarbon groups may have include, but are not limited to, a halogen atom, an oxo group, a hydroxyl group, a substituted oxy group (e.g., an alkoxy group, an aryloxy group, an acyloxy group), a carboxyl group, a substituted oxycarbonyl group, a substituted or unsubstituted carbamoyl group, a cyano group, a nitro group, a substituted or unsubstituted amino group, an alkyl group (e.g., methyl, ethyl, and other $C_1-C_4$ alkyl groups), a cycloalkyl group, an aryl group (e.g., phenyl, or naphthyl group), and a heterocyclic group. The preferred hydrocarbon groups include, for example, alkyl groups each having about 1 to 30 carbon atoms, and aromatic hydrocarbon groups (especially, phenyl or naphthyl group) each having about 6 to 14 carbon atoms. The substituted oxy groups include, but are not limited to, alkoxy groups, aryloxy groups and aralkyloxy groups.

Typical examples of the organic salts (ii) include organic ammonium salts, organic phosphonium salts, organic sulfonium salts and other organic onium salts. Concrete examples of organic ammonium salts include tetramethylammonium chloride, tetraethylammonium chloride, tetrabutylammonium chloride, tetrahexylammonium chloride, trioctylmethylammonium chloride, triethylphenylammonium chloride, tributyl(hexadecyl)ammonium chloride, di(octadecyl)dimethylammonium chloride, and other quaternary ammonium chlorides, and corresponding quaternary ammonium bromides, and other quaternary ammonium salts each having four hydrocarbon groups bonded to its nitrogen atom; dimethylpiperidinium chloride, hexadecylpyridinium chloride, methyl quinolinium chloride, and other cyclic quaternary ammonium salts. Practical examples of the organicphosphonium salts include tetramethylphosphonium chloride, tetrabutylphosphonium chloride, tributyl (hexadecyl)phosphonium chloride, triethylphenylphosphonium chloride, and other quaternary phosphonium chlorides, and corresponding quaternary phosphonium bromides, and other quaternary phosphonium salts each having four hydrocarbon groups bonded to its phosphorus atom. Concrete examples of the organic sulfonium salts include triethylsulfonium iodide, ethyldiphenylsulfonium iodide, and other sulfonium salts each having three hydrocarbon groups bonded to its sulfur atom.

The organic salts (ii) also include methanesulfonic acid salts, ethanesulfonic acid salts, octanesulfonic acid salts, dodecanesulfonic acid salts, and other alkyl-sulfonic acid salts (e.g., $C_6$–$C_{18}$ alkyl-sulfonic acidsalts); benzenesulfonic acid salts, p-toluenesulfonic acid salts, naphthalenesulfonic acid salts, decylbenzenesulfonic acid salts, dodecylbenzenesulfonic acid salts, and other aryl-sulfonic acid salts which may be substituted with an alkyl group (e.g., $C_6$–$C_{18}$ alkyl-arylsulfonic acid salts); sulfonic acid type ion exchange resins (ion exchangers); and phosphonic acid type ion exchange resins (ion exchangers).

The amount of the organic salt (ii) falls in the range, for example, from about 0.0001 to 0.7 mole, preferably from about 0.001 to 0.5 mole, more preferably from about 0.002 to 0.1 mole, and often from about 0.005 to 0.05 mole relative to 1 mole of the substrate.

In the invented process, the presence of t-butyl hydroperoxide (TBHP) and other peroxides in a reaction system can enhance or promote the reaction to significantly increase the yield of a target compound. The proportion of the peroxide is, for example, about 0.0001 to 0.2 mole, preferably about 0.001 to 0.1 mole, and more preferably about 0.003 to 0.05 mole relative to 1 mole of the substrate.

[Sulfur Oxide and Oxygen]

The sulfur oxides can be shown by the formula $S_xO_y$, wherein x is an integer of 1 or 2 and y is an integer of 1 to 7. In compounds of the formula, when x is 1, y is usually an integer of 1 to 4, and when x is 2, y is generally 3 or 7.

Such sulfur oxides include, but are not limited to, SO, $S_2O_3$, $SO_2$, $SO_3$, $S_2O_7$, and $SO_4$. Each of these sulfur oxides can be used alone or in combination.

Preferred sulfur oxides include those mainly containing at least one selected from sulfur dioxide ($SO_2$) and sulfur trioxide ($SO_3$). The sulfur oxide can be used in combination with oxygen. For example, a combination use of sulfur dioxide ($SO_2$) with oxygen can yield a corresponding sulfonic acid in high yield. The oxygen may be either pure oxygen or oxygen diluted with an inert gas such as carbon dioxide, nitrogen, helium, or argon. The oxygen source can also be air. As the sulfur trioxide, fuming sulfuric acid containing sulfur trioxide can be employed.

The proportion of the sulfur oxide can be selected according to the proportion of sulfur acid radicals (e.g., sulfonate radical, sulfinate radical) introduced into the organic substrate, and is for example about 1 to 50 moles, and preferably about 1.5 to 30 moles relative to 1 mole of the substrate. The reaction can be performed in a sulfur oxide atmosphere in large excess. When sulfur dioxide ($SO_2$) or another sulfur oxide is used in combination with oxygen, the ratio of the two components is such that the former/the latter (molar ratio) is about 1/99 to 99/1, and preferably the former/the latter (molar ratio) is about 10/90 to 90/10, and more preferably the former/the latter (molar ratio) is about 30/70 to 70/30.

[Organic Substrate]

The substrates for use in the invention are not critical and include a wide variety of saturated or unsaturated compounds. Such compounds include, but are not limited to, hydrocarbons (aliphatichydrocarbons, alicyclichydrocarbons, aromatic hydrocarbons), heterocyclic compounds, alcohols, ethers, esters, ketones, and aldehydes.

Examples of preferred substrates include (a) isocyclic (carbocyclic) or heterocyclic compounds each having a methylene group, (b) compounds each having a methine carbon atom, and (c) compounds each having a methyl group or a methylene group at the adjacent position to an unsaturated bond. In these compounds, a sulfur acid radical (e.g., sulfonate radical, sulfinate radical) is introduced into the aforementioned methyl group, methylene group or methine carbon atom.

Of the compounds (a), isocyclic compounds (a1) having a methylene group include, but are not limited to, cycloalkanes (e.g., cyclopropane, cyclobutane, cyclopentane, cyclohexane, methylcyclohexane, 1,2-diethylcyclohexane, isopropylcyclohexane, cycloheptane, cyclooctane, methylcyclooctane, cyclononane, cyclodecane, cyclododecane, cyclotridecane, cyclotetradecane, cyclopentadecane, cyclohexadecane, cyclooctadecane, cyclononadecane, and other $C_3$–$C_{30}$ cycloalkanes), cycloalkenes (e.g., cyclopropene, cyclobutene, cyclopentene, cyclohexene, 1-methyl-1-cyclohexene, cycloheptene, cyclooctene, cyclononene, cyclodecene, cyclododecene, and other $C_3$–$C_{30}$ cycloalkenes), cycloalkadienes (e.g., cyclopentadiene, cyclohexadiene, cycloheptadiene, cyclooctadiene, cyclodecadiene, cyclododecadiene, and other $C_5$–$C_{30}$ cycloalkadienes), cycloalkatrienes, cycloalkatetraenes, and condensed polycyclic aromatic hydrocarbons each having a 5- to 8-membered non-aromatic ring condensed therewith.

Heterocyclic compounds (a2) having a methylene group of the compounds (a) include, for example, 5- or 6-membered cyclic compounds having a hetero atom selected from nitrogen, oxygen and sulfur atoms, or condensed heterocyclic compounds having an aromatic ring and a 5- or 6-membered ring having a hetero atom condensed to the aromatic ring. Examples of such heterocyclic compounds (a2) are dihydrofuran, tetrahydrofuran, pyran, dihydropyran, tetrahydropyran, piperidine, piperazine, pyrrolidine, and xanthene. In the compounds (a), a sulfur acid radical is introduced into the methylene group constituting a non-aromatic ring.

The compounds (b) having a methine carbon atom (methylidyne group) include, for example, (b1) chain hydrocarbons each having a tertiary carbon atom, (b2) bridged cyclic compounds, and (b3) non-aromatic cyclic compounds each having a hydrocarbon group bonded to its ring.

The chain hydrocarbons (b1) each having a tertiary carbon atom include, but are not limited to, isobutane, isopentane, isohexane, 3-methylpentane, 2,3-dimethylbutane, 2-methylhexane, 3-methylhexane, 2,3-dimethylpentane, 2,4-dimethylpentane, 2,3,4-trimethylpentane, 3-ethylpentane, 2,3-dimethylhexane, 2,4-dimethylhexane, 3,4-dimethylhexane, 2,5-dimethylhexane, 2-propylhexane, 2-methylheptane, 4-methylheptane, 2-ethylheptane, 3-ethylheptane, 2,6-dimethylheptane, 2-methyloctane, 3-methyloctane, 2,7-dimethyloctane, 2-methylnonane, and other aliphatic hydrocarbons each having about 4 to 20 (preferably about 4 to 10) carbon atoms. In the compounds (b1), a sulfur acid radical is introduced into the tertiary carbon atom.

Examples of the bridged cyclic compounds (b2) are decalin, bicyclo[2.2.0]hexane, bicyclo[2.2.2]octane, bicyclo[3.2.1]octane, bicyclo[4.3.2]undecane, thujone, carane, pinane, pinene, bornane, bornylene, norbornane, norbornene, camphor, camphoric acid, camphene, tricyclene, tricyclo[4.3.1.1$^{2,5}$]undecane, tricyclo[5.2.1.0$^{3,8}$]decane, exotricyclo[5.2.1.0$^{2,6}$]decane, endotricyclo[5.2.1.0$^{2,6}$]decane, endotricyclo[5.2.2.0$^{2,6}$]undecane, adamantane, 1-adamantanol, 1-chloroadamantane, 1-methyladamantane, 1,3-dimethyladamantane, 1-methoxyadamantane, 1-carboxyadamantane, 1-methoxycarbonyladamantane, 1-nitroadamantane, tetracyclo[4.4.0.1$^{2,5}$.1$^{7,10}$]dodecane, perhydroanthracene, perhydroacenaphthene, perhydrophenanthrene, perhydrophenalene, perhydroindene, quinuclidine, and other bicyclic, tricyclic or tetracyclic bridged hydrocarbons or bridged heterocyclic compounds and derivatives of these compounds. These bridged cyclic compounds (b2) each have a methine carbon atom at a bridgehead position (corresponding to a junction position when two rings commonly possess two atoms), and a sulfur acid radical is introduced into the methine carbon atom.

Illustrative non-aromatic cyclic compounds (b3) each having a hydrocarbon group bonded to its ring include 1-methylcyclopentane, 1-methylcyclohexane, limonene, menthene, menthol, carvomenthone, menthone, and other alicyclic hydrocarbons each having 3 to 15 members and having a hydrocarbon group (e.g., an alkyl group)each having 1 to 20 (preferably 1 to 10) carbon atoms bonded to its ring, and derivatives of these compounds. In these compounds (b3), a sulfur acid radical is introduced into a methine carbon atom at a bonding site between the constitutive ring and the hydrocarbon group.

The compounds (c) each having a methyl group or a methylene group at the adjacent position to an unsaturated bond include (c1) organic compounds each having a methyl group or a methylene group at the adjacent position to a non-aromatic carbon-carbon double bond and/or triple bond, (c2) compounds each having a methyl group or a methylene group at the adjacent position to an aromatic ring, and (c3) compounds each having a methyl group or a methylene group at the adjacent position to a carbonyl group.

The compounds (c1) include, but are not limited to, chain unsaturated hydrocarbons each having about 3 to 12 carbon atoms, such as propylene, 1-butene, 2-butene, butadiene, 1-pentene, 2-pentene, isoprene, 1-hexene, 2-hexene, 1,5-hexadiene, 2,3-dimethyl-2-butene, 3-hexene, 1-heptene, 2-heptene, 1,6-heptadiene, 1-octene, 2-octene, 3-octene, 1,7-octadiene, 2,6-octadiene, 2-methyl-2-butene, 1-nonene, 2-nonene, decene, decadiene, dodecene, dodecadiene, dodecatriene, undecene, undecadiene, and undecatriene. In these compounds (c1), a sulfur acid radical is introduced into, for example, a carbon atom at an allylic position.

Examples of the compounds (c2) are toluene, xylene, mesitylene, durene, ethylbenzene, propylbenzene, cumene, methylethylbenzene, methylnaphthalene, dimethylnaphthalene, methylanthracene, dimethylanthracene, trimethylanthracene, dibenzyl, diphenylmethane, triphenylethane, and other aromatic hydrocarbons each having an alkyl group; and methylfuran, methylchroman, methylpyridine (picoline), dimethylpyridine (lutidine), trimethylpyridine (collidine), ethylpyridine, methylquinoline, methylindole, indan, indene, tetralin, fluorene, and other heterocyclic compounds each having an alkyl group. In these compounds (c2), a sulfur acid radical is introduced into a so-called benzylic position.

The compounds (c3) include, for example, aldehydes, ketones, carboxylic acids and derivatives thereof. Such aldehydes include, but are not limited to, aliphatic aldehydes (e.g., acetaldehyde, propionaldehyde, butyraldehyde, isobutyl aldehyde, pentyl aldehyde, hexyl aldehyde, heptyl aldehyde, octyl aldehyde, nonyl aldehyde, decyl aldehyde, and other $C_2$–$C_{12}$ alkyl monoaldehydes, malonaldehyde, succinaldehyde, adipaldehyde, sebacaldehyde, and other aliphatic polyaldehydes), alicyclic aldehydes (e.g., formylcyclohexane, and cycloneral), and heterocyclic aldehydes.

The ketones include, but are not limited to, aliphatic ketones (e.g., acetone, methyl ethyl ketone, methyl isopropyl ketone, methyl isobutyl ketone, methyl t-butyl ketone, 2-pentanone, 3-pentanone, 2-hexanone, 3-hexanone, 2-heptanone, 3-heptanone, 4-heptanone, 2-octanone, 3-octanone, 4-octanone, 2-nonanone, and 2-decanone), cyclic ketones (e.g., cyclopentanone, cyclohexanone, methylcyclohexanone, dimethylcyclohexanone, cycloheptanone, isophorone, cyclooctanone, cyclononanone, cyclodecanone, cyclohexadione, cyclooctadione, and other non-aromatic cyclic mono- or poly-ketones, α-tetralone, β-tetralone, indanone, and other cyclic ketones each having an aromatic ring), bridged cyclic ketones (e.g., adamantanone, methyladamantanone, and dimethyladamantanone), aromatic ketones (e.g., acetophenone, and propiophenone), and heterocyclic ketones (e.g., inden-1-one, and fluoren-9-one).

The carboxylic acids and derivatives thereof include, for example, aliphatic dicarboxylic acids and derivatives thereof (e.g., malonic acid and its esters, succinic acid and its esters, glutaric acid and its esters) In the compounds (c3), a sulfur acid radical is introduced into, for example, a so-called active methylene group or methyl group.

These substrates may have an appropriate substituent. Such substituents include, but are not limited to, halogen atoms, alkyl groups, alkenyl groups, alkynyl groups, cycloalkyl groups, aryl groups, aralkyl groups, acyl groups, hydroxyl group, alkoxy groups, acyloxy groups, mercapto group, carboxyl group, alkoxycarbonyl group, amino group, N-substituted amino groups, carbamoyl group, N-substituted carbamoyl groups, nitro group, cyano group, sulfonyl group, sulfinyl group, phosphino group, and heterocyclic groups.

[Reaction]

A reaction can be performed in the presence of, or in the absence of, a solvent. Such solvents include, but are not limited to, hexane, octane, and other aliphatic hydrocarbons; benzene and other aromatic hydrocarbons; dichloromethane, chloroform, dichloroethane, dichlorobenzene, and other halogenated hydrocarbons; t-butanol, t-amyl alcohol, and other alcohols; acetonitrile, benzonitrile, and other nitriles; acetic acid, propionic acid, and other organic acids; formamide, acetamide, dimethylformamide (DMF), dimethylacetamide, and other amides; and mixtures of these solvents.

The invented process is distinguishable from conventional equivalents in that sulfonation and other reactions can smoothly proceed even under relatively mild conditions. A reaction temperature can be selected within the range from about 0° C. to about 150° C., preferably from about 10° C. to about 125° C., and more preferably from about 15° C. to about 100° C. The reaction can be performed either under atmospheric pressures or under pressure, in any system such as a batch system, a semi-batch system or a continuous system.

The reaction can yield an organic sulfur acid such as sulfonic acid and sulfinic acid corresponding to the substrate. For example, the combination use of sulfur dioxide and oxygen or the use of sulfur trioxide can produce sulfonic acid in good yield. The formed organic sulfur acid can be converted into a corresponding salt of organic sulfur acid according to conventional techniques. For example, such salts can be obtained by reacting the organic sulfur acid with alkali metal hydroxides, alkali metal carbonates, alkali metal hydrogencarbonates, alkaline earth metal hydroxides, alkaline earth metal carbonates, amines, or thioureas (isothioureas) in an appropriate solvent such as water.

After the completion of the reaction, reaction products can be easily separated and purified in a conventional manner such as filtration, concentration, distillation, extraction, crystallization, recrystallization, column chromatography and other separation means, or any combination of these separation means.

As described above, the invented process employs the combination of an imide compound of the formula (1) and a sulfur oxide and can efficiently produce an organic sulfur acid or its salt under relatively mild conditions. The invented process can also efficiently yield an organic sulfur acid or its salt directly from a corresponding non-aromatic hydrocarbon.

The present invention will now be illustrated in more detail with reference to several inventive examples below, which are not intended to limit the scope of the invention.

EXAMPLE 1

A mixture of 2 mmol of adamantane, 0.2 mmol of N-hydroxyphthalimide, 0.01 mmol of vanadyl acetylacetonato [VO(acac)$_2$], and 5 ml of acetic acid was stirred at 60° C. in a sulfur dioxide (SO$_2$) (0.5 atm) and oxygen (0.5 atm) atmosphere for 1 hour. A gas chromatographic analysis of a reaction mixture revealed that the conversion rate of adamantane was 91% and that a trace amount of 2-adamantanone was formed. The reaction mixture was extracted with water, was neutralized with an aqueous sodium hydroxide solution, and was adjusted to weak acidity with hydrochloric acid. An aqueous benzyl isothiourea hydrochloride solution in large excess was then added to the mixture to separate S-benzyl thiuronium salt of 1-adamantanesulfonic acid. The yield of this compound was 32%.

EXAMPLE 2

A mixture of 2 mmol of adamantane, 0.2 mmol of N-hydroxyphthalimide, 0.01 mmol of vanadyl acetylacetonato [(VO(acac)$_2$], and 5 ml of acetic acid was stirred at 40° C. in a sulfur dioxide (SO$_2$) (0.5 atm) and oxygen (0.5 atm) atmosphere for 2 hours. A gas chromatographic analysis of a reaction mixture revealed that the conversion rate of adamantane was 63% and that 2-adamantanone was formed in a yield of 7%. The reaction mixture was extracted with water, was neutralized with an aqueous sodium hydroxide solution, and was adjusted to weak acidity with hydrochloric acid. An aqueous benzyl isothiourea hydrochloride solution in large excess was then added to the mixture to separate S-benzyl thiuronium salt of 1-adamantanesulfonic acid. The yield of this compound was 40%.

EXAMPLE 3

A mixture of 2 mmol of adamantane, 0.2 mmol of N-hydroxyphthalimide, 0.01 mmol of vanadyl acetylacetonato [VO(acac)$_2$], 0.02 mmol of TBHP (t-butyl hydroperoxide), and 5 ml of acetic acid was stirred at 25° C. in a sulfur dioxide (SO$_2$) (0.5 atm) and oxygen (0.5 atm) atmosphere for 20 hours. A gas chromatographic analysis of a reaction mixture revealed that the conversion rate of adamantane was 53% and that 2-adamantanone was formed in a yield of 3%. The reaction mixture was extracted with water, was neutralized with an aqueous sodium hydroxide solution, and was adjusted to weak acidity with hydrochloric acid. An aqueous benzyl isothiourea hydrochloride solution in large excess was then added to the mixture to separate S-benzyl thiuronium salt of 1-adamantanesulfonic acid. The yield of this compound was 40%.

EXAMPLE 4

A mixture of 2 mmol of cyclooctane, 0.2 mmol of N-hydroxyphthalimide, 0.01 mmol of vanadyl acetylacetonato [VO(acac)$_2$], and 5 ml of acetic acid was stirred at 40° C. in a sulfur dioxide (SO$_2$) (0.5 atm) and oxygen (0.5 atm) atmosphere for 2 hours. A gas chromatographic analysis of a reaction mixture revealed that the conversion rate of cyclooctane was 54%. The reaction mixture was extracted with water, was neutralized with an aqueous sodium hydroxide solution, and was adjusted to weak acidity with hydrochloric acid. An aqueous benzyl isothiourea hydrochloride solution in large excess was then added to the mixture to separate S-benzyl thiuronium salt of cyclooctanesulfonic acid. The yield of this compound was 15%.

EXAMPLE 5

A mixture of 2 mmol of cyclooctane, 0.2 mmol of N-hydroxyphthalimide, 0.01 mmol of vanadyl acetylacetonato [VO(acac)$_2$], 0.02 mmol of TBHP, and 5 ml of acetic acid was stirred at 40° C. in a sulfur dioxide (SO 2) (0.5 atm) and oxygen (0.5 atm) atmosphere for 5 hours. A gas chromatographic analysis of a reaction mixture revealed that the conversion rate of cyclooctane was 80%. The reaction mixture was extracted with water, was neutralized with an aqueous sodium hydroxide solution, and was adjusted to weak acidity with hydrochloric acid. An aqueous benzyl isothiourea hydrochloride solution in large excess was then added to the mixture to separate S-benzyl thiuronium salt of cyclooctanesulfonic acid. The yield of this compound was 23%.

EXAMPLE 6

A mixture of 2 mmol of cyclohexane, 0.2 mmol of N-hydroxyphthalimide, 0.01 mmol of vanadyl acetylacetonato [VO(acac)$_2$], 0.02 mmol of TBHP, and 5 ml of acetic acid was stirred at 40° C. in a sulfur dioxide (SO$_2$) (0.5 atm) and oxygen (0.5 atm) atmosphere for 5 hours. The reaction mixture was extracted with water, was neutralized with an aqueous sodium hydroxide solution, and was adjusted to weak acidity with hydrochloric acid. An aqueous benzyl isothiourea hydrochloride solution in large excess was then added to the mixture to separate S-benzyl thiuronium salt of cyclohexanesulfonic acid. The yield of this compound was 11%.

Other embodiments and variations will be obvious to those skilled in the art, and this invention is not to be limited to the specific matters stated above.

What is claimed is:

1. A process for producing an organic sulfur acid or its salt, said process comprising the step of reacting a sulfur oxide with an organic substrate in the presence of an imide compound of the following formula (1):

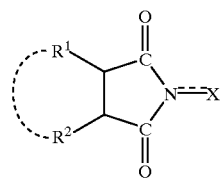
(I)

wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond or an aromatic or non-aromatic ring; X is an oxygen atom or a hydroxyl group, where one or two N-substituted cyclic imido groups indicated in the formula (1) may be further bonded to the aforementioned $R^1$, $R^2$ or to the double bond or aromatic or non-aromatic ring formed together by $R^1$ and $R^2$, to yield a corresponding organic sulfur acid or its salt.

2. A process according to claim 1, wherein said sulfur oxide mainly comprises at least one selected from sulfur dioxide and sulfur trioxide.

3. A process according to claim 1, wherein said organic substrate is one selected from the group consisting of (a) isocyclic or heterocyclic compounds each having a methylene group, (b) compounds having a methine carbon atom, and (c) compounds each having a methyl group or a methylene group at the adjacent position to an unsaturated bond.

* * * * *